United States Patent [19]
Budai et al.

[11] Patent Number: 4,587,261
[45] Date of Patent: May 6, 1986

[54] CYCLOALKANE DERIVATIVES AND FODDER COMPOSITIONS CONTAINING THE SAME

[75] Inventors: Zoltán Budai; Pál Benkó; Ildikó Rátz née Simonek; Éva Rákóczy née Pintér; Károly Magyar; József Kelemen; Attila Mándi, all of Budapest, Hungary

[73] Assignee: Egyt Gyogyszervegyeszeti Gyar, Budapest, Hungary

[21] Appl. No.: 491,083

[22] Filed: May 3, 1983

[30] Foreign Application Priority Data

May 4, 1982 [HU] Hungary .................. 1380/82

[51] Int. Cl.$^4$ .............. C07C 125/065; C07C 125/067; A61K 31/27
[52] U.S. Cl. .................. 514/542; 514/614; 560/27; 560/24; 564/36; 564/149
[58] Field of Search .......... 560/27, 24; 564/36, 564/149; 426/623, 635; 514/542, 614

[56] References Cited

U.S. PATENT DOCUMENTS 4,236,017 11/1980 Boschi .................. 560/27 X

FOREIGN PATENT DOCUMENTS 1085028 7/1954 France .................. 564/149

*Primary Examiner*—Bernard Helfin
*Attorney, Agent, or Firm*—Karl F. Ross; Herbert Dubno

[57] ABSTRACT

The invention relates to new cycloalkane derivatives, a process for the preparation thereof and compositions—particularly feed additives and animal feeds—containing the same.

The new compounds of the present invention correspond to the general formula I $$\underset{R-\underset{\underset{H}{|}}{\overset{\overset{C-R^2}{|}}{C}}-R^1}{(CH_2)_n\ \ C=N-NH-\underset{\underset{O}{\|}}{C}-R^3} \quad I$$

wherein
n is 3, 4, 5 or 6;
R denotes a phenyl group optionally carrying one or more substituent/s/ selected from the group consisting of halogen, lower alkoxy and lower alkyl;
$R^1$ and $R^2$ each represent hydrogen or form together a valence bond;
$R^3$ represents lower alkoxy or a phenyl optionally substituted by one or more $C_{1-12}$ alkoxy.

The fodder additives and fodders according to the invention contain as active ingredient an amount of 1 ppm to 85% by weight of a compound of the general formula I in admixture with inert solid or liquid carriers or diluents and can be used to advantage in animal husbandry.

8 Claims, No Drawings

CYCLOALKANE DERIVATIVES AND FODDER COMPOSITIONS CONTAINING THE SAME

This invention relates to new cycloalkane derivatives, a process for the preparation thereof and compositions—particularly feed additives and animal feeds—containing the same.

According to the present invention there are provided new cycloalkane derivatives of the formula I $$\begin{array}{c}(CH_2)_n \quad C=N-NH-C-R^3 \\ \phantom{xxxxx} \| \\ \phantom{xxxxxxxxxxxxxxxx} O \\ C-R^2 \\ | \\ R-C-R^1 \\ | \\ H\end{array} \quad \text{I}$$

wherein
n is 3, 4, 5 or 6;
R denotes a phenyl group which can have one or more substituents selected from the group consisting of halogen, lower alkoxy and lower alkyl;
$R^1$ and $R^2$ each represent hydrogen or form together a valence bond;
$R^3$ represents lower alkoxy or a phenyl optionally substituted by one or more $C_{1-12}$ alkoxy.

The term "lower alkyl" used in the specification and claims refers to straight-chained or branched saturated aliphatic hydrocarbyl groups containing 1 to 4 carbon atoms (e.g. methyl, ethyl, n-propyl, isopropyl, n-butyl). The term "$C_{1-12}$ alkoxy" relates to straight-chained or branched alkylether groups having 1 to 12 carbon atoms, e.g. methoxy, ethoxy, n-propoxy, n-butoxy, n-hexyloxy, decyloxy, isopropoxy. The term "halogen" encompasses all the four halogen atoms, such as fluorine, chlorine, bromine and iodine. The term "lower alkylene" relates to alkylene groups containing 1 to 4 carbon atoms (e.g. methylene or ethylene group). The "$C_{3-7}$ cycloalkylidene" is preferably cyclopentylidene or cyclohexylidene.

n is preferably 4 or 5, so the compounds of the formula I are preferably cyclohexane or cycloheptane derivatives.

$R^3$ may represent a phenyl group carrying optionally one or more $C_{1-12}$ alkoxy substituents (e.g. 3,4,5-trimethoxyphenyl). $R^3$ is preferably a methoxy group.

The symbols $R^1$ and $R^2$ preferably form together a valence bond.

A particularly preferred representative of the compounds of the formula I is the N-(p-methoxycarbonyl)-N'-[2-/p-methoxyphenylmethylene/-cyclohexylidene]-hydrazine.

The compounds of the formula I with acidic character can form salts with bases. The salt formation is carried out in a known way. The alkali salts (e.g. sodium or potassium salts), the alkaline-earth salts (e.g. calcium or magnesium salts) and the salts formed with biologically acceptable organic bases (such as triethylamine, dimethylamine, dimethylaniline) are particularly preferred.

According to a further feature of the invention there is provided a process for the preparation of compounds having the formula I characterized by
a. reacting a ketone of the formula II $$\begin{array}{c}(CH_2)_n \quad C=A \\ \phantom{xxxxx} \\ C-R^2 \\ | \\ R-C-R^1 \\ | \\ H\end{array} \quad \text{II}$$

wherein
A denotes an oxygen or a sulfur atom and n, R, $R^1$ and $R^2$ are as defined above,
or a reactive derivative thereof, with a hydrazine derivative of the general formula III $$H_2N-NH-C-R^3 \quad \text{III}$$
$$\phantom{xxxxxxxx}\|$$
$$\phantom{xxxxxxxx}O$$

wherein $R^3$ is as defined above, or with a reactive derivative thereof formed on the amino group; or
b. reacting a ketone of the formula II, wherein A, n, R, $R^1$ and $R^2$ have the same meanings as above, with hydrazine of the formula IV $$H_2N-NH_2 \quad \text{IV}$$

or with an acid addition salt thereof, and reacting the compound of the formula V thus obtained $$\begin{array}{c}(CH_2)_n \quad C=N-NH_2 \\ \phantom{xxxxx} \\ C-R^2 \\ | \\ R-C-R^1 \\ | \\ H\end{array} \quad \text{V}$$

after or without isolation—with a compound of the formula VI $$Hlg-C-R^3 \quad \text{VI}$$
$$\phantom{xxxx}\|$$
$$\phantom{xxxx}O$$

wherein Hlg represents halogen.

According to method (a) of the invention a ketone of the formula II is reacted with a hydrazine derivative of the formula III. Preferably ketones of the formula II, wherein A stands for an oxygen atom, are used as the starting substance. The compounds of the formulae II and III are preferably reacted in an equimolar amount, but a slight excess of any of the starting substances may also be used. The reaction may be performed in an organic solvent. For this purpose any inert solvent dissolving the starting substances is suitable. As reaction medium preferably aromatic hydrocarbons (e.g. benzene, toluene, xylene) or alcohols (e.g. methanol, ethanol, isopropanol) can be used. The reaction is preferably carried out under heating, between 40° C. and the boiling point of the reaction mixture. One proceeds preferably at about the boiling point of the reaction mixture.

The compounds of the formula I can be isolated from the reaction mixture by known methods (e.g. crystallization or evaporation).

The ketones of the formula II and/or the hydrazine derivatives of the formula III may be used in the form of the reactive derivatives thereof as well. Among the reactive derivatives of the ketones of the general formula II the ketals of the formula VII

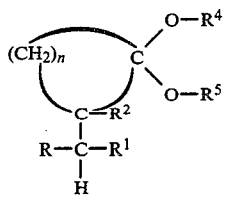

wherein
$R^5$ and $R^4$ each represent a lower alkyl group or together form a lower alkylene group, and n, R, $R^1$ and $R^2$ are as defined above,
are mentioned. These ketals are preferably dimethyl, diethyl or ethylene ketals. The reaction can be performed between 20° C. and 200° C., in an inert solvent. As reaction medium preferably aromatic hydrocarbons (e.g. benzene, toluene or xylene) can be used. The reaction may be carried out in the presence of catalytic amounts of a strong acid. For this purpose hydrogen chloride, hydrogen bromide, p-toluenesulfonic acid, etc. can be used.

Instead of the compounds of the formula III the reactive derivatives thereof formed on the amino group can also be used. These derivatives correspond to the formula VIII

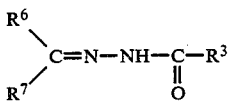

wherein $R^7$ stands for hydrogen, lower alkyl or phenyl and $R^6$ is hydrogen or lower alkyl, or $R^7$ and $R^6$ form, together with the adjacent carbon atom to which they are attached, a 3 to 7 membered cycloalkylidene ring, with the proviso that at least one of $R^6$ and $R^7$ is other than hydrogen. The reaction can be performed at a temperature between about 20° C. and 200° C., in an inert solvent. As reaction medium organic solvents inert toward the reaction and dissolving properly the starting substances (e.g. alcohols, such as methanol, ethanol; esters, such as ethyl acetate, etc) may be used. The reaction is performed in the presence of catalytic amounts of a strong acid. For this purpose e.g. hydrogen chloride, hydrogen bromide, sulfuric, phosphoric, trifluoroacetic or p-toluenesulfonic acid may be used.

According to method (b) of the invention a compound of the formula II is reacted with hydrazine of the formula IV or with an acid addition salt thereof, then the thus-obtained compound of the formula V is reacted, after or without isolation, with a compound of the formula VI. The first step of this reaction is preferably performed between room temperature and 60° C., in an inert solvent. As reaction medium preferably alcohols (e.g. methanol or ethanol) can be used. Instead of the hydrazine of the formula IV in certain cases an acid addition salt thereof (e.g. the hydrochloride or sulfate) is used. According to a preferred embodiment of this process the compound of the formula II is reacted with hydrazine dihydrochloride in the presence of 1 molar equivalent of a base. For this purpose inorganic bases (e.g. alkali hydroxides, carbonates or hydrogen carbonates, preferably sodium hydroxide or potassium hydrogen carbonate) or organic bases (e.g. triethyl amine) may be used.

The thus-obtained compound of the formula V is reacted with the haloformic acid derivative of the formula VI after or without isolation, preferably without isolation. It is preferable to use compounds of the formula VI, wherein Hlg is chlorine. The reaction is carried out in the presence of an acid binding agent. For this purpose the aforesaid inorganic or organic bases may serve.

The compounds of the formula I, wherein $R^1$ and $R^2$ form together a valence bond, are preferably prepared by methods according to this invention wherein no acidic catalyst is used. So when using the reactive derivatives of the starting substances of the formulae II and III and carrying out the reaction in the presence of catalytic amounts of a strong base preferably the compounds of the formula I, wherein $R^1$ and $R^2$ each represent hydrogen, are prepared. The compounds of the formula I, wherein $R^1$ and $R^2$ form together a valence bond, are preferably produced according to method (a) of the invention, that is by the interaction of the compounds of the formulae II and III.

The starting substances used for the synthesis according to the invention are in part commercial products or compounds known from the literature or can be prepared by methods known per se.

The new compounds of the formula I can be used in animal husbandry due to their weight gain increasing properties.

The weight gain increasing effect of the new compounds of the formula I is shown in the following test.

Pigs are used as test animals. For each dose groups of 6 animals are used. The pigs of the test group are fed with a fodder comprising 50 mg/kg of the test compound of the formula I and reference compound (Flavomicine), respectively. The animals of the control group receive the same fodder but without test compound of the formula I.

The animals in each test group are fed with the same fodder and under identical conditions except the art and amount of the test compound incorporated into the fodder. The results obtained are summarized in Table I.

TABLE I

| Test compound (Example No.) | Average daily weight gain, related to the controls | Weight of fodder producing 1 kg of weight gain, related to the controls |
|---|---|---|
| 2 | 132% | 78% |
| Flavomicine | 114% | 96% |
| Control | 100% | 100% |

The weight gain increasing effect of the compounds of the formula I is also tested on weaned lambkins. Each test group consists of 10 animals. The active ingredient content of the fodder is 50 mg/kg, the animals are fed with the fodder for a period of 40 days. Each test is repeated three times. The results are summarized in Table II.

TABLE II

| Test compound (Example No.) | Average daily weight gain, related to the controls | Amount of fodder producing a weight gain of 1 kg | |
|---|---|---|---|
| | | kg | % of the controls |
| 2 | 116.0 | 3.65 | 91.7 |
| 4 | 105.3 | 3.80 | 95.5 |
| Control | 100.0 | 3.98 | 100.0 |

It appears from the above data that the weight gain of the animals fed with a fodder containing the compounds of the invention is significantly greater than that of the pigs of the control group. At the same time the same weight gain can be achieved with a considerably smaller amount of fodder when a compound of the formula I is incorporated into the animal feed. This is a proof of an improved fodder utilization.

According to a further feature of the invention there are provided compositions—particularly fodder additives and fodders—comprising as active ingredient an amount of 1 ppm to 85% by weight of a compound of the formula I, wherein n, R, $R^1$, $R^2$ and $R^3$ are as defined above, in admixture with inert solid or liquid carriers or diluents.

According to a further feature of the invention there is provided a process for the preparation of fodder additives and fodders, characterized by admixing a compound of the formula I, wherein n, R, $R^1$, $R^2$ and $R^3$ are as defined above, or a biologically acceptable salt thereof, with suitable edible solid or liquid carrier or diluent or additive generally used in the production of fodder additives and fodders.

As carrier or diluent any substance of vegetable or animal origin applicable in the feeding of animals or serving as fodder can be used. For this purpose e.g. wheat, barley, maize, soybean, oats, rye, alfalfa, can be used in appropriate forms (grits, groats, meal, bran, etc.), furthermore fish meal, meat meal, bone meal or mixtures thereof can be applied as well. One may advantageously use a fiber-free green plant fodder concentrate with high protein content (e.g. VEPEX ®).

As additives e.g. silicic acid, antioxidants, starch, dicalcium phosphate, calcium carbonate, sorbic acid, etc. can be used. As wetting agent e.g. non-toxic oils, preferably soybean oil, maize oil or mineral oil can be applied. Various alkylene glycols can also be used as wetting agent. The starch used may be wheat, maize or potato starch.

The fodder additives and concentrates may contain usual vitamins (e.g. vitamin A, $B_1$, $B_2$, $B_3$, $B_6$, $B_{12}$, E, K) and trace elements (e.g. Mn, Fe, Zn, Cu, I), too.

The active ingredient content of the compositions may vary within wide ranges. The fodder additives may contain about 5 to 80% by weight, preferably about 10 to 50% by weight, particularly about 20 to 50% by weight of the active ingredient of the formula I. The active ingredient content of the animal fodders ready for use may be about 1 to 400 ppm, preferably about 10 to 100 ppm.

The fodder additives and concentrates are diluted with suitable fodder components or are incorporated into suitable animal feeds to provide animal feeds ready for use.

The fodders according to the present invention can be used for the increase of weight gain of various domestic animals, such as pigs, lambs, cattle and poultry, particularly pigs.

Further details of the present invention are to be found in the following examples without limiting the scope of the invention to the examples.

EXAMPLE 1

Preparation of N-(methoxycarbonyl)-N'-(2-phenylmethylenecyclohexylidene)-hydrazine To a solution of 37.2 g (0.2 moles) of 2-phenylmethylenecyclohexan-1-one in 200 ml of anhydrous ethanol a solution of 18.0 g (0.2 moles) of N-methoxycarbonyl hydrazine in 40 ml of anhydrous ethanol is added, under stirring. The reaction mixture is boiled for a short while, then cooled, clarified with activated carbon, filtered and the filtrate is cooled. The separated white crystals are filtered off and dried. 50.63 g of the desired compound are obtained. Yield: 98%.

M.P.: 170°–171° C.

Analysis ($C_{15}H_{18}N_2O_2$) Mol. weight: 258.33. Calculated: C%=69.8, H%=7.00, N%=10.82. Found: C%=69.22, H%=7.2, N%=10.94.

UV absorption $\lambda_{max}$=288 nm. $E_{1cm}^{1\%}$=636.24. ($\epsilon$=16000).

EXAMPLE 2

Preparation of N-(methoxycarbonyl)-N'-[2-(p-methoxyphenylmethylene)-cyclohexylidene]-hydrazine To a solution of 22.68 g (0.252 moles) of N-methoxycarbonyl hydrazine in 100 ml of benzene a solution of 50.0 g (0.23 moles) of 2-(p-methoxyphenylmethylene)-cyclohexan-1-one in 300 ml of anhydrous methanol is added, under stirring. The reaction mixture is boiled for one hour, clarified with activated carbon, filtered and the filtrate is cooled. 63.05 g of the desired compound are obtained. Yield: 94.65%.

M.p.: 162°–163° C.

Analysis ($C_{16}H_{20}N_2O_3$) Mol. weight: 288.35. Calculated: C%=66.7, H%=6.94, N%=9.73. Found: C%=66.47, H%=6.85, N%=9.71.

UV absorption $\lambda_{max}$=301 nm. ($\epsilon$=20600). $E_{1cm}^{1\%}$=720.

EXAMPLE 3

Preparation of N-(methoxycarbonyl)N'-(2-phenylmethylenecycloheptylidene)-hydrazine 9.0 g (0.1 mole) of N-methoxycarbonyl hydrazine are dissolved in 250 ml of anhydrous ethanol, under stirring, and 20.0 g (0.1 mole) of 2-phenylmethylenecycloheptan-1-one are added to the solution. The reaction mixture is kept at the boiling point under stirring, thereafter clarified with activated carbon, filtered and the filtrate is crystallized. 24.78 g of the named compound are obtained. Yield: 91%.

M.p.: 143°–145° C.

Analysis ($C_{16}H_{20}N_2O_2$) Mol. weight=272.35. Calculated: C%=70.60, H%=7.35, N%=10.39. Found: C%=71.0, H%=7.59, N%=10.25.

UV absorption $\lambda_{max}$=275 nm. ($\epsilon$=1600). $E_{1cm}^{1\%}$=588.

EXAMPLE 4

Preparation of
N-(methoxycarbonyl)-N'-[2-(p-chlorophenylmethylene)-cyclohexylidene]-hydrazine 33.32 g (0.151 moles) of 2-(p-chlorophenylmethylene)-cyclohexan-1-one and 13.5 g (0.151 moles) of N-methoxycarbonyl hydrazine are dissolved in 230 ml of isopropanol. The reaction mixture is boiled for a few hours, then cooled, clarified with activated carbon, filtered, the filtrate is cooled and the separated crystals are filtered off. 41.2 g of the named compound are obtained. Yield: 93.2%. M.p.: 160.5°–162° C.

Analysis ($C_{15}H_{17}ClN_2O_2$) Mol. weight=292.77. Calculated: C%=61.70, H%=5.8, N%=9.6. Found: C%=61.95, H%=6.0, N%=9.7.

UV absorption $\lambda_{max}$=293 nm. ($\epsilon$=18500). $E_{1cm}^{1\%}$=635.

EXAMPLE 5

Preparation of
N-(methoxycarbonyl)-N-[2-(2',6'-dichlorophenylmethylene)-cyclohexylidene]-hydrazine 25.52 g (0.1 mole) of 2-(2',6'-dichlorophenylmethylene)cyclohexan-1-one and 9.0 g (0.1 mole) of N-methoxycarbonyl hydrazine are dissolved in 150 cm³ of anhydrous ethanol, and the solution is boiled for 3 hours. Then it is clarified with activated carbon, filtered, the filtrate is cooled, and the separated crystals are filtered off. 28.47 g (87%) of the named compound are obtained.

Analysis: ($C_{15}H_{16}Cl_2N_2O_2$) Mol. weight=327.20. Calculated: C%=55.06, H%=4.93, Cl%=21.67, N%=8.56. Found: C%=55.21, H%=4.9, Cl%=21.58, N%=8.55.

EXAMPLE 6

Preparation of
N-(methoxycarbonyl)-N'-[2-(3',4'-dimethoxyphenylmethylene)-cyclohexylidene]-hydrazine 24.63 g (0.1 mole) of 2-(3',4'-dimethoxyphenylmethylene)cyclohexan-1-one and 9.0 g (0.1 mole) of N-methoxycarbonyl hydrazine are dissolved in 150 cm³ of methanol, and the solution is boiled for 2 hours. Then it is cooled and the crystals are filtered off. 21.87 g (68.7%) of the named compound are obtained.

Analysis: ($C_{17}H_{22}N_2O_4$) Mol. weight=318.37. Calculated: C%=64.13, H%=6.97, N%=8.8. Found: C%=63.85, H%=6.77, N%=8.78.

EXAMPLE 7

Preparation of
N-(methoxycarbonyl)-N'-(2-benzylcyclohexylidene)-hydrazine 18.83 g (0.1 mole) of 2-benzylcyclohexan-1-one and 9.0 g (0.1 mole) of N-methoxycarbonyl hydrazine are dissolved in 100 cm³ of anhydrous ethanol, and the solution is boiled for 2 hours. Then it is cooled, and the separated crystals are filtered off. 18.2 g (96.9%) of the named compound are obtained.

Analysis: ($C_{15}H_{20}N_2O_2$) Mol. weight=260.33. Calculated: C%=69.2, H%=7.74, N%=10.76. Found: C%=69.0, H%=7.52, N%=10.75.

EXAMPLE 8

Preparation of
N-(3,5-dimethoxy-4-hexyloxybenzoyl)-N'-[2'-(phenylmethylene)-cyclohexylidene]-hydrazine To a solution of 29.6 g (0.1 mole) of 3,5-dimethoxy-4-hexyloxybenzoic acid hydrazide in 110 cm³ of anhydrous ethanol a solution of 18.6 g (0.1 mole) of 2-phenylmethylenecyclohexan-1-one in 50 cm³ of ethanol is added. The reaction mixture is boiled for one hour, cooled and filtered. 36.35 g (78.2%) of the named compound are obtained. M.p.: 158°–160° C.

Analysis: ($C_{28}H_{36}N_2O_4$) Mol. weight=464.59. Calculated: C%=72.38, H%=7.81, N%=6.03. Found: C%=72.10, H%=7.70, N%=6.00.

EXAMPLE 9

Preparation of
N-(3,4,5-trimethoxybenzoyl)-N'-[(2'-phenylmethylene)-cyclohexylidene)]-hydrazine To a solution of 22.6 g (0.1 mole) of 3,4,5-trimethoxybenzoic acid hydrazide in 220 cm³ of anhydrous ethanol a solution of 18.6 g (0.1 mole) of 2-phenylmethylenecyclohexan-1-one in 90 cm³ of anhydrous ethanol is added. The reaction mixture is boiled for one hour, cooled, filtered and the filtrate is dried. 26.94 g (68.3%) of the named compound are obtained. M.p.: 181°–182° C.

Analysis: ($C_{23}H_{26}N_2O_4$) Mol. weight: 394.46. Calculated: C%=70.03, H%=6.64, N%=7.10. Found: C%=69.8, H%=6.52, N%=7.08.

EXAMPLE 10

Preparation of
N-(3,5-dimethoxy-4-decyloxybenzoyl)-N'-[(2'-phenylmethylene)-cyclohexylidene]-hydrazine To a solution of 17.6 g (0.05 moles) of 3,5-dimethoxy-4-decyloxybenzoic acid hydrazide in 100 cm³ of anhydrous ethanol a solution of 9.3 g (0.05 moles) of 2-phenylmethylenecyclohexan-1-one in 40 cm³ of anhydrous ethanol is added. The reaction mixture is boiled for 2 hours, cooled and the separated crystals are filtered off. Yield: 18.85 g (72.4%).

M.p.: 161°–162° C.

Analysis: ($C_{32}H_{44}N_2O_4$) Mol. weight: 520.69. Calculated: C%=73.81, N%=5.52, N%=5.38. Found: C%=74.02, H%=8.70, N%=5.36.

EXAMPLE 11

Preparation of
N-(3,5-dimethoxy-4-butoxybenzoyl)-N'-[(2'-(phenylmethylene)-cyclopentylidene]-hydrazine To a solution of 26.8 g (0.1 mole) of 3,5-dimethoxy-4-butoxybenzoic acid hydrazide in 200 cm³ of anhydrous ethanol a solution of 17.2 g (0.1 mole) of 2-phenylmethylenecyclopentan-1-one in 50 cm³ of anhydrous ethanol is added. The reaction mixture is boiled for one hour, cooled, the separated crystals are filtered off and dried. 35.3 g (83.8%) of the title compound are obtained. Yield: 83.8%. M.p.: 226°–227° C.

Analysis: ($C_{25}H_{30}N_2O_4$) Mol. weight=422.53. Calculated: C%=71.07, H%=7.16, N%=6.63. Found: C%=70.86, H%=7.32, N%=6.66.

UV $\lambda_{max}$=328 nm. ($\epsilon$=30200).

EXAMPLE 12

Preparation of
N-(3,5-dimethoxy-4-ethoxybenzoyl)-N'-[(2-phenylmethylenecyclopentylidene)]-hydrazine A solution of 30.2 g (0.126 moles) of 3,5-dimethoxy-4-ethoxybenzoic acid hydrazide in 250 cm$^3$ of anhydrous ethanol is added to a solution of 21.8 g (0.126 moles) of 2-phenylmethylenecyclopentan-1-one in 50 cm$^3$ of ethanol. The reaction mixture is boiled for one hour, then cooled. The separated crystals are filtered off and dried. Yield: 39.78 g (80.0%). M.p.: 239°–240° C.

Analysis: ($C_{23}H_{26}N_2O_4$) Mol. weight=394.48. Calculated: C%=70.03, H%=6.64, N%=7.1. Found: C%=69.85, H%=6.72, N%=6.98.

UV $\lambda_{max}$=330 nm. ($\epsilon$=29974).

EXAMPLE 13

Preparation of
N-(3,5-dimethoxy-4-butoxybenzoyl)-N'-[(2'-phenylmethylene)-cyclohexylidene]-hydrazine To a solution of 12.5 g (0.045 moles) of 3,5-dimethoxy-4-butoxybenzoic acid hydrazide in 150 cm$^3$ of anhydrous ethanol a solution of 9.3 g (0.05 moles) of 2-phenylmethylenecyclohexan-1-one in 100 cm$^3$ of anhydrous ethanol is added. The reaction mixture is boiled for one hour, then cooled and the separated crystals are filtered off. Yield: 12.38 g (63%) of the named compound. M.p.: 180°–181° C.

Analysis: ($C_{26}H_{32}N_2O_4$) Mol. weight=436.56. Calculated: C%=71.6, H%=7.34, N%=6.42. Found: C%=71.56, H%=7.6, N%=6.52.

UV $\lambda_{max}$=299 nm. ($\epsilon$=1970).

EXAMPLE 14

Preparation of
N-(3,5-dimethoxy-4-ethoxybenzoyl)-N'-[(2'-phenylmethylene)-cyclohexylidene]-hydrazine To a solution of 24.0 g (0.1 mole) of 3,5-dimethoxy-4-ethoxybenzoic acid hydrazide in 200 cm$^3$ of anhydrous ethanol a solution of 18.6 g (0.1 mole) of 2-phenylmethylenecyclohexan-1-one in 200 cm$^3$ of anhydrous ethanol is added. The reaction mixture is boiled for one hour, cooled, the crystals are filtered off and dried. 26.5 g (65%) of the named compound are obtained. M.p.: 176°–177° C.

Analysis: ($C_{24}H_{28}N_2O_4$) Mol. weight=408.40. Calculated: C%=70.57, H%=6.91, N%=6.86. Found: C%=70.24, H%=7.2, N%=6.72.

UV $\lambda_{max}$=299 nm. ($\epsilon$=20380).

EXAMPLE 15

A premix for supplementing pig fodder is prepared with the following composition:

| Components | Amounts |
| --- | --- |
| Vitamin A | 3,000,000 IU |
| Vitamin D$_3$ | 600,000 IU |
| Vitamin E | 4,000 IU |
| Vitamin K$_3$ | 400 mg |
| Vitamin B$_1$ | 600 mg |
| Vitamin B$_2$ | 800 mg |
| Vitamin B$_3$ | 2,000 mg |
| Vitamin B$_6$ | 800 mg |
| Vitamin B$_{12}$ | 10 mg |
| Niacin | 4,000 mg |
| Choline chloride | 60,000 mg |
| Active agent according to Example 7 | 10,000 mg |
| Butylhydroxytoluene (antioxidant) | 30,000 mg |
| Flavoring substances | 8,000 mg |
| Sodium saccharate | 30,000 mg |
| Trace elements: | |
| Mn | 8,000 mg |
| Fe | 30,000 mg |
| Zn | 20,000 mg |
| Cu | 6,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 16

A premix for supplementing piglet fodder is prepared with the following composition:

| Components | Amounts |
| --- | --- |
| Vitamin A | 1,200,000 IU |
| Vitamin D$_3$ | 300,000 IU |
| Vitamin E | 2,000 IU |
| Vitamin B$_2$ | 600 mg |
| Vitamin B$_3$ | 2,000 mg |
| Vitamin B$_{12}$ | 5 mg |
| Niacin | 3,000 mg |
| Choline chloride | 40,000 mg |
| Active agent according to Example 7 | 10,000 mg |
| Butylhydroxytoluene (antioxidant) | 30,000 mg |
| Trace elements: | |
| Mn | 6,000 mg |
| Fe | 10,000 mg |
| Zn | 15,000 mg |
| Cu | 30,000 mg |
| I | 100 mg |
| Twice-ground bran ad | 1,000 g |

This premix of vitamins and trace elements is admixed with the basal fodder in a concentration of 0.5 kg per 100 kg.

EXAMPLE 17

0.5 kg of a premix as described in Example 15 are admixed with 100.0 kg of a basal fodder with the following composition:

| Components | Amounts, kg |
| --- | --- |
| Maize | 37.6 |
| Barley | 25.4 |
| Wheat | 6.0 |
| Oats | 5.0 |
| Soybean | 13.0 |
| Fish meal | 6.0 |
| Bran | 2.4 |
| Fat powder | 1.5 |
| Premix of minerals[x] | 1.0 |
| Lime (fodder quality) | 1.0 |
| Sodium chloride (fodder quality) | 0.5 |
| Biolisine | 0.1 |
| Premix according to Example 15 | 0.5 |
| Total weight: | 100.0 kg |

The active agent content of the resulting pig fodder is 50 ppm.

*The composition of the premix of minerals is as follows:

| Components | Amounts, % |
|---|---|
| Dicalcium phosphate | 55.0 |
| Monocalcium phosphate | 40.0 |
| Calcium carbonate | 5.0 |

EXAMPLE 28

0.5 kg of a premix as described in Example 16 are admixed with 100.0 kg of a basal fodder with the following composition:

| Components | Amounts, kg |
|---|---|
| Maize | 25.0 |
| Wheat | 34.0 |
| Extracted soybean | 18.0 |
| Milk powder | 9.9 |
| Fish meal | 4.0 |
| Yeast (fodder quality) | 2.0 |
| Fat powder | 3.4 |
| Premix of minerals according to Example 16 | 1.8 |
| Lime (fodder quality) | 1.0 |
| Sodium chloride (fodder quality) | 0.4 |
| Premix according to Example 16 | 0.5 |
| Total weight: | 100.0 kg |

The active agent content of the resulting piglet fodder is 50 ppm.

EXAMPLE 19

400 kg of a pre-ground soybean meal are filled into a mixer, 3.1 kg of soybean oil are added under stirring, and the mixture is stirred until the solids are coated with oil. Thereafter 9.1 kg of an active agent according to Example 2 are added and the mixture is stirred until a homogeneous blend is obtained. Finally 9.0 kg of soybean oil are added, and the mixture is homogenized again.

EXAMPLE 20

0.5 kg of an active agent according to Example 2 are added to 40 kg of corn meal under stirring, and simultaneously 3.0 kg of propylene glycol are sprayed into the mixture. Thereafter 1.4 kg of dicalcium phosphate are added and the mixture is homogenized.

EXAMPLE 21

10 kg of alfalfa meal and 15 kg of VEPEX® are stirred for 20 hours, thereafter 1 kg of maize oil is started to spray into the mixture with an even speed so that spraying is continued during the introduction of the following additional components: 2.5 kg of an active agent according to Example 1, 10 kg of maize starch, 2.5 kg of the above active agent, 0.3 kg of silicon dioxide, 0.6 kg of ascorbic acid, 9 kg of maize starch and 2.5 kg of the above active agent. Thereafter the mixture is stirred for additional 5 minutes.

EXAMPLE 22

One proceeds as described in Example 19 with the difference that butylene glycol is applied as wetting agent instead of soybean oil.

EXAMPLE 23

A. 3.5 kg of potato starch are admixed with 2.9 kg of an active agent according to Example 2. 0.05 kg of mineral oil are sprayed into the mixture, thereafter 0.2 kg of sorbic acid, 0.4 kg of silicon dioxide and 0.1 kg of calcium propionate are added, and the mixture is stirred for additional 2 minutes.

B. 4.2 kg of fish meal are admixed with 22 kg of rye bran, 0.6 kg of mineral oil are sprayed into the mixture, thereafter 4 kg of a mixture prepared according to point A., 10 kg of maize meal, 4 kg of a mixture prepared according to point A. and 9 kg of maize meal are introduced under stirring. Finally 0.6 kg of mineral oil are sprayed into the mixture.

EXAMPLE 24

100 kg of wheat bran, 10 kg of an active agent according to Example 3, 2.5 kg of calcium carbonate, 0.15 kg of α-tocopherol and 0.4 kg of calcium propionate are homogenized with 4 kg of propylene glycol.

EXAMPLE 25

10 kg of soybean meal and 0.6 kg of an active agent according to Example 3 are homogenized with 2.5 kg of butylene glycol.

EXAMPLE 26

50 kg of soybean meal, 6 kg of an active agent according to Example 4, 0.5 kg of silicon dioxide and 0.2 kg of calcium propionate are homogenized with 1.6 kg of soybean oil.

What we claim is:

1. A cycloalkene compound of the formula I $$(CH_2)_n \underset{C-R^2}{\overset{C=N-NH-\underset{O}{\overset{\parallel}{C}}-R^3}{\diagup}}$$
$$R-\underset{H}{\overset{|}{C}}-R^1$$

(I)

wherein
n is 3, 4, 5 or 6;
R is phenyl which can have one or more substituents selected from the group consisting of halogen, lower alkoxy and lower alkyl;
$R^1$ and $R^2$ each are hydrogen or form together a valence bond;
$R^3$ is lower alkoxy or a phenyl which can be substituted with one or more $C_{1-12}$ alkoxy.

2. A compound as defined in claim 1 wherein $R^3$ is for methoxy.

3. A compound as defined in claim 1 wherein $R^1$ and $R^2$ form together a valence bond.

4. N-(Methoxycarbonyl)-N'-2-(p-methoxyphenylmethylene)-cyclohexylidene-hydrazine as defined in claim 1.

5. A fodder having weight-gain increasing effect comprising as active ingredient an amount of 1 ppm to 85% by weight of a compound as defined in claim 1 in admixture with a suitable inert solid or liquid carrier or diluent.

6. The fodder having weight-gain increasing effect defined in claim 5 wherein said compound is N-(methoxycarbonyl)-N'-{2-(p-methoxy-phenylmethylene)-cyclohexylidene}-hydrazine.

7. The fodder having weight-gain increasing effect defined in claim 5, comprising as a carrier a substance of vegetable or animal origin applicable in the feeding of animals or serving as fodder, selected from the group which consists of wheat, oats, maize, soybean, rye, or alfalfa in the form of grits, groats or meal, furthermore fish meal or meat meal.

8. A method for improving the weight gain and fodder utilization of an animal, which comprises feeding said animal with the composition of claim 5.

* * * * *